(12) United States Patent  
Chalmers

(10) Patent No.: US 7,294,346 B2
(45) Date of Patent: Nov. 13, 2007

(54) MEDICATION DELIVERY DEVICE

(75) Inventor: Anne-Marie Chalmers, Osprey, FL (US)

(73) Assignee: Ambo Innovations LLC, Osprey, FL (US)

( * ) Notice: Subject to any disclaimer, the term of this patent is extended or adjusted under 35 U.S.C. 154(b) by 792 days.

(21) Appl. No.: 10/787,278

(22) Filed: Feb. 26, 2004

(65) Prior Publication Data

US 2005/0053650 A1    Mar. 10, 2005

Related U.S. Application Data

(63) Continuation-in-part of application No. 10/657,521, filed on Sep. 8, 2003, now abandoned, and a continuation-in-part of application No. 10/690,387, filed on Oct. 21, 2003, now abandoned.

(51) Int. Cl.
*A61K 9/20* (2006.01)
*A61K 9/48* (2006.01)

(52) U.S. Cl. ........................................ 424/464; 424/451

(58) Field of Classification Search .................... None
See application file for complete search history.

(56) References Cited

U.S. PATENT DOCUMENTS

2006/0003000 A1 *   1/2006   Solomon et al. ............ 424/464

* cited by examiner

*Primary Examiner*—S. Tran
(74) *Attorney, Agent, or Firm*—Lahive & Cockfield, LLP; Jane E. Remillard, Esq.; Brian C. Trinque

(57) ABSTRACT

A medication delivery device by virtue of which multiple medications are produced in various medication delivery device forms, including particularly pill, capsule, gel-cap or soft gel form, which medication delivery device forms are readily identifiable by color or shape, and which medication delivery device forms are connected and affixed one to another, though the use of a bonding material, glue or adhesive, in a chain, train or string fashion, thus presenting to the patient that which appears to be only one item for ingestion or insertion into a live body, without the use or employment of any biodegradable outer container intended for ingestion or insertion into a live body, into which outer container the said various pills might have otherwise been inserted, and with said connection and affixation being intentionally separable to facilitate ingestion or to enable intentional selective removal of one or more connected or affixed components.

2 Claims, 1 Drawing Sheet

MEDICATION DELIVERY DEVICE

CROSS-REFERENCE TO RELATED APPLICATIONS

This Application is a Continuation-in-Part of application Ser. No. 10/657,521 entitled Medication Delivery Device, filed by the same sole inventor as herein with the United States Patent and Trademark Office on Sep. 8, 2003, now abandoned which application is; and is also a Continuation-in-Part of application Ser. No. 10/690,387, filed by the same sole inventor as herein with the United States Patent and Trademark Office on Oct. 21, 2003, now abandoned which application is; and is also a Continuation-in-Part of application Ser. No. 10/785,903, filed by the same sole inventor as herein with the United States Patent and Trademark Office on Feb. 24, 2004, which application is pending.

STATEMENT REGARDING FEDERALLY SPONSORED RESEARCH OR DEVELOPMENT

Not Applicable

REFERENCE TO SEQUENCE LISTING, A TABLE OR A COMPUTER PROGRAM LISTING COMPACT DISK APPENDIX

Not Applicable

BACKGROUND OF INVENTION

This invention relates to a device for the simultaneous delivery into a live body of multiple medication products, pharmaceuticals, nutritional products and inert materials.

Most medications presently ingested by patients contain significant amount of inert materials or fillers. These inert materials are generally present due to the concentrated nature, and thus small volume, of the actual active ingredient in the medication. If only the active ingredient was presented to a patient, it would be of a size which was too small for the patient to comfortably handle, resulting in either the patient dropping or losing the medication or the patient ingesting an overdose of the medication.

As used herein, the words "pill", "tablet", "capsule", "gel cap" and "soft-gel" are used interchangeably (unless the context at any section hereof otherwise dictate to the contrary, or unless specifically otherwise limited in scope at a particular section hereof), and encompass all other mechanisms and means for delivery of medication products into a live body, including but not necessarily limited to pills, tablets, capsules, gel caps or soft-gels.

As used herein, "Pill" means and includes pills, tablets, capsules, gel caps, soft gels and all other mechanisms and means for delivery of medication products to a live body.

As used herein, the words "medication product" includes and encompasses, but is not limited to, prescription drugs, non-prescription drugs, over-the-counter drugs, nutritional supplements and inert "filler" materials used in conjunction with any of the foregoing.

As used herein, the words "container" and "containment means" includes and encompasses not only the traditional medication capsule, pill, gel cap, soft-gel, suppositories, skin patches and sublingual applications, but also includes and encompasses any and all other medication delivery mechanisms and means.

As used herein, the words "outer contained" means the container or containment means which contains multiple medication products as pills, capsules, gel-caps, soft gels, or liquids, but which itself is not connected with or affixed to another or further container or containment device in chain, train or string fashion, and which is not itself sequentially imbedded within another container, and which said non-connected and non-affixed container or containment means can be ingested or inserted into a live body.

Many studies show that age is strongly correlated to the number of prescription medication Pills a person is taking. Due to a continually increasingly aging population and increased use of drug therapy, more and more older people find themselves often taking several (perhaps as many as 4 to 10) Pills for treating or preventing illnesses every day. Research has shown that even patients for whom strict adherence to prescribed drug regimens is crucial, rates of non-compliance can still range from as much as 20% to 50%.

Each year in the United States, the consequences of poor compliance cost an estimated $100 billion in added health care expenses, lost productivity, and other direct and indirect costs, in addition to personal suffering.

Another consequence of people having to take several Pills every day, is that it increases the risk of mix-ups, for example, the patient becomes confused as to whether they have taken their medications or not. It is then possible that they take too much or too little of their medications; this results in side effects from drugs more likely to happen.

It is sadly ironic that the more confused the patient is, the more likely it is that they have even more Pills to keep track of and monitor.

According to the United States Food and Drug Administration, 1.5 million Americans were hospitalized in 1978 alone as a consequence of pharmaceutical drugs administered to "cure" them, It was found that some 30% of all hospitalized people suffered further damage from the therapy prescribed to them.

Side effects involving prescription drugs are the fifth leading cause of deaths in the USA.

One means of increasing compliance is to reduce the number of Pills taken per day, thus reducing patient resistance to swallowing large numbers of Pills or the possibility of patients forgetting to take some of their medication, thus reducing the number of Pills taken per day, and reducing the risk of medication-induced error.

Moreover, numerous studies have shown that certain combinations of different substances or medications can dramatically improve the health outcomes through additional or synergic effects. But these combinations most often require the ingestion of more Pills which may again lower the compliance.

The delivery of medication products, including prescription drugs, over-the-counter drugs, nutritional supplements and inert materials, has been traditionally accomplished by the use of Pills.

Typically Pills are comprised of the active ingredient compounded with inert ingredients for various purposes, including ease of handling small amounts of active ingredients. When the said mixture of active and inactive ingredients is then compressed to form a "pill", that pill typically is then coated or covered with a polished "surface" substance functioning as both a physical/chemical barrier and as a helper for smooth swallowing. Very often medications can come in a dose of only a few milligrams, but since this amount is so small and unmanageable, the size of the pill has to be increased substantially with fillers Similarly, capsules, gel caps and soft-gels are composed of an outer material or casing which is dissolved after ingestion by the patient. The interior portion of the capsule, gel caps or soft-gel is filled with an active ingredient compounded with inert ingredients for various purposes, including ease of handling of small amounts of active ingredients, similar to a pill as described above.

There are several distinctions between capsules vis-à-vis soft gels or gel caps. The major difference between a capsule and a soft gel or gel cap is that a capsule is a hard shell and a soft gel or gel cap is physically a softer gelatin container. A soft gel or gel cap is essentially a capsule made from gelatin, usually from a bovine or pig source, although there are also available soft gels made from vegetable sources, e.g., potato starch. A capsule, on the other hand, is generally made from many different materials, including gelatin formulations. Capsules usually contain solid materials such as powders, although they occasionally do contain liquids, whereas soft gels or gel caps usually contain oils or liquid, although some soft gels or gel caps do contain rather powdery substances in soft gels or gel caps, which facilitate the swallowing process.

A sub-category or variation of gel caps is "liquid gel caps". The interior of these gel caps are filled with liquid rather than solid materials, typically a blend of active and inactive ingredients. The liquid gel caps provide an easy means of carrying liquid medications for ingestion without the need to transport the liquid from a liquid container to the mouth of the patient. Thus the risk of liquid bottle spillage or breakage is avoided.

The disadvantage of a typical prescription Pill is that it usually contain only one primary medication thus only addresses one type of indication or problem.

The treatment of many seriously ill or chronic patients requires the use of multiple medications. Many patients find having to take numerous traditional Pills is burdensome and restrictive, and causes additional responsibility and worries. Not only is the patient burdened with multiple containers for the various medications, but the patient must also track each Pill to assure that they have in fact timely ingested the proper dosage of each such medication.

To generate a "tracking system", it is well known many patients hesitate to switch to cheaper generic substances, because patients use, for example, the heart shaped form of medication for one ailment or the soothing shade of sky blue color of medication for another ailment to help them recognize their medication. The pharmaceutical industry brands their drug products by offering them in a wide array of different shapes, sizes and colors. Although this helps the patient to recognize their numerous individual Pills, but it also makes prescription medication treatment more expensive than necessary. This is due not only to production and marketing costs but also because the patients are hesitant to try unrecognizable generic versions.

The present invention reflects the fact that: (1) Most people do not experience any problems swallowing oblong capsules up to the size of eight (8) mm in diameter and twenty (20) mm to twenty five (25) mm in length, although this size is somewhat larger than most of the prescription Pills on the market; (2) Keeping track of one large Pill is easier than keeping track of numerous small Pills; (3) Many prescription drugs come in Pill sizes larger than chemically necessary and the active ingredient is often so minute it needs to be sized up with fillers to become manageable for the consumer, or it needs to fit a specific shape for marketing purposes; and (4) There are presently no national or international standards for sizes, shapes or colors for Pills; instead even the same generic component can come in a variety of appearances to reflect the manufacturers brand. This makes it confusing and difficult for the patient to switch from one manufacturer to another for the same medication.

Combining the fact that it is physically possible to add many prescription drugs together in one ingestible unit, and still maintain a Pill size which is easier to swallow, opens up the possibility of solving the above compliance problems and reducing the risk of taking too much or little medication.

An objective of the present invention is to solve the aforesaid problems, including by reducing the number of Pills that will contain the originally intended, prescribed or recommended medications and doses, thus increasing compliance and reducing the possibility of confusion.

A further objective of the present invention is also to solve the aforesaid problems by is that by facilitating a switch, in certain instances, to relatively less expensive generic products.

A yet further objective of the present invention is also to solve the aforesaid problems by enabling a world wide patient individualized manufacturing systems/fulfillment centers/pharmacies based on international standards for size and configuration of Pills.

BRIEF SUMMARY OF THE INVENTION

A medication delivery device by virtue of which multiple medications are, in one embodiment, produced in separate, sometimes coated, Pill form, preferably re-formulated with minimal inactive ingredients to minimize the size of each Pill, which Pills are then connected and affixed one to another in a chain, train or string fashion, thus presenting to the patient a "multiple medication assemblage" which appears to be one item for ingestion or insertion into a live body, without the use or employment of any outer container for the containment of the said various mutually affixed Pills.

The various medication devices which are the components of a Pill assemblage, assembled in chain, train or string fashion, are removably combined and affixed to each other using an adhesive means, including glue (including gelatin based glue). The patient is thus enabled to selectively remove and delete certain components of the medication dose, to thereby facilitate ingestion by making the ingestion unit a smaller size, with the unit size to be determined by the patient, by the patient adjusting the unit length.

Alternatively, the said various multiple medication Pills need not be re-formulated to minimize inactive ingredients, in which event the overall size of the said multiple medication assemblage would not be minimized and the effectiveness of the said multiple medication assemblage would not be maximized.

The nature and mechanism of said connection and affixation of the several Pills in the multiple medication assemblage is an affixation means, including bonding material, glue or adhesive.

The said connection or affixation of the several pills in the multiple medication assemblage is designed to enable the intentional separation of the said various medication pill components of the said multiple medication assemblage to thereby allow and enable a patient to selectively reduce the size of the multiple medication assemblage, or to selectively remove certain identified medication components of the multiple medication assemblage which the patient was otherwise to ingest or insert.

Each of the said Pills included in the said multiple medication assemblage is preferably formed in a distinctive color or shape for ready recognition and identification as between each other.

The active ingredients in each of the said Pills is not in actual physical contact with the active ingredients of the adjoining pills because of the surface barrier between each of them provided by the coating on each pill, or by the physical structure of the outer surface of the capsule, gel-cap or soft gel.

The diameter of each Pill in the multiple medication assemblage can vary, but the maximum adhesion with adjoining Pills will be accomplished if the said Pill diameters are relatively uniform.

The thickness of each Pill in the multiple medication assemblage will vary depending upon the amount of active ingredient of the particular medication is in a specific Pill

BRIEF DESCRIPTION OF THE DRAWINGS

These FIG. 1 through FIG. 4 are not necessarily exhaustive of all embodiments of the invention.

DETAILED DESCRIPTION OF THE INVENTION

A medication delivery device, as exemplified by several preferred embodiments depicted in FIGS. 1 through 4, provides for the delivery to a living body, human or animal, of a maximum amount of active ingredients, with a minimum amount of inert materials, of multiple medication products simultaneously.

Although the more typical method and means for entry into the said living body is by ingestion, the invention also encompasses other forms of such entry, including but not limited to suppository form.

Figure 1:
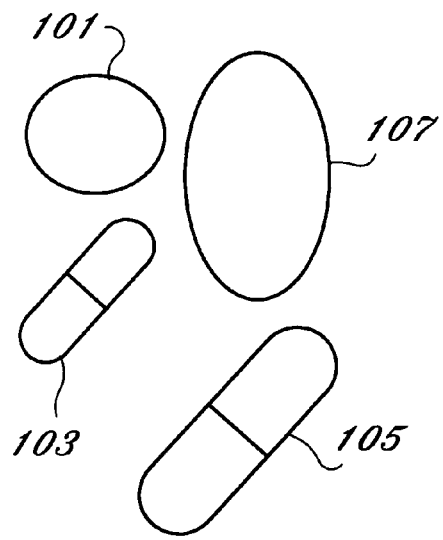
FIG. 1 is a depiction of an unassembled array of different medications, depicted for illustration purposes as one pill, two capsules of different sizes, and a gel cap.

As depicted in FIG. 1, a patient who is prescribed numerous medication products is not infrequently confronted with a plurality and a variety of means for delivery of each such medication, including a pill (101), a small capsule (103), a large capsule (105) and a gel cap (107).

Figure 2:
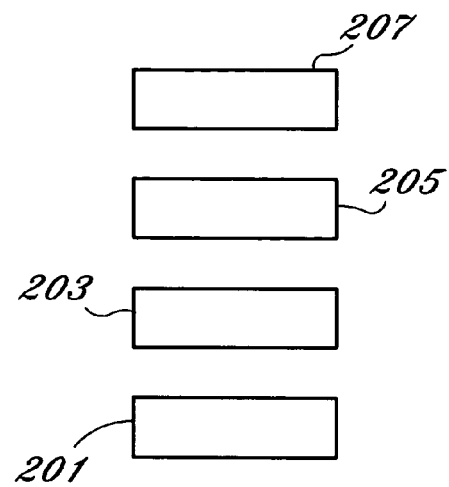
FIG. 2 is a depiction of the medications which had been depicted in FIG. 1, but with those medications shown in FIG. 2 as now being in pill form, with each pill being of a particular shape and size, with the diameter of each such pill being relatively uniform and the thickness of each such pill varying and being dependent upon the dosage of the active ingredient of medication of which each such pill is comprised.
Figure 4:
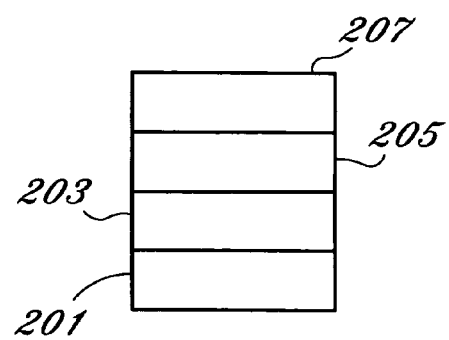
FIG. 4 is a depiction of the medications which had been depicted in FIG. 2 now being connected or affixed to one another in chain, train or string fashion.

The present invention encompasses and includes reformulating medications into pill form as depicted in FIG. 2, and then connecting or affixing the various pills one to another in chain, train or string fashion, as depicted in FIG. 4.

The means of connecting and affixing the several medication delivery devices to each other includes glue and other bonding agents and materials.

Figure 3:
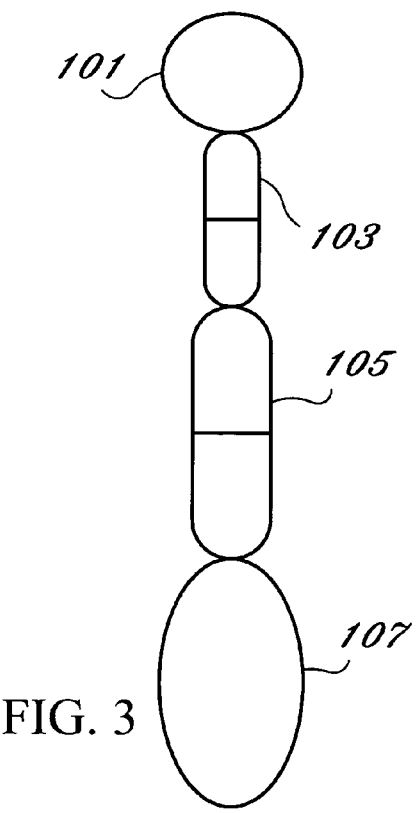
FIG. 3 is a depiction of the medications which had been depicted in FIG. 1 now being connected or affixed to one another in chain, train or string fashion.

The present invention also encompasses and includes the use of medications in the form of capsules, gel-cap and soft gels, in addition to pills, connected or affixed one to another in chain, train or string fashion, as depicted in FIG. 3.

The pill (101), small capsule (103), large capsule (105) and gel cap (107) of FIG. 1 are depicted in FIG. 3 connected and affixed to one another. In this regard, the particular order or sequence of such connection or affixation is irrelevant.

The present invention encompasses and includes reformulating medication products into Pill form to minimize inactive ingredients, thus reducing the physical volume of each such Pill, and shaping and configuring the physical outer appearance of each such medication product, as exemplified in FIG. 2, which FIG. 2 depicts the medication products which had been depicted in FIG. 1 as (101), (103), (105) and (107) in newly shaped and sized pill forms depicted in FIG. 2 as (201), (203), (205) and (207), respectively.

This can also be accomplished using capsules, gel-caps or soft gels.

FIG. 4 depicts the said newly shaped and sized pills which had been depicted in FIG. 2, but now connected or affixed one to another in chain, train or string fashion. A consequence of using medications in pill form of similar sizes is that the said connection or affixation is thereby maximally effective.

The diameter of each said pill (201), (203), (205) and (207) is essentially the same, with that diameter having a minimum measurement consistent with the capabilities of pharmaceutical manufacturing equipment and a maximum measurement consistent with the size of a Pill of medication easily swallowed by a living body in the category of living bodies to which the particular medication is applicable, or easily inserted as a suppository into the appropriate orifice of a living body in the category of living bodies to which the particular medication is applicable.

As capsule with a diameter of eight (8) mm and a length of twenty (20) mm to twenty five (25) mm is generally considered to reflect the maximum comfortable size of Pill for oral ingestion by human adults.

Although the foregoing embodiments refer to pills, the invention is not limited to pills as specifically shown and discussed herein, but rather encompasses any and all medication containers and containment means, including pills, gel caps, capsules and soft gels.

In addition, although several of the preferred embodiments described hereinbefore are comprised, for illustration purposes, of a specific number of Pills, the invention is not limited to a specific number of Pills, but rather encompasses any number of such medication delivery devices connected or affixed one to another in chain, train or string fashion.

The active ingredients contained within each Pill are separated from the other active ingredients contained within pills to which they are connected or affixed by the coatings on the pills, or by the physical structure of the capsule, gel-cap or soft gel, thereby preventing the medication substance in one such Pill from mixing with the medication substance in the other connected or affixed Pill. Consequently, there is no concern about the medication substances starting to react with each other, and the medications substances will therefore not represent a new chemical compound, before being ingested or otherwise delivered into a live body.

The highly economically attractive and flexible prospect of different medication substances actually being produced at locations distant from each other and then being consolidated in medication delivery devices in accordance with this invention become feasible, and indeed economically attractive.

The numerous advantages of this invention include: (a) The ability to maintain the chemical stability of the different medication substances, by preventing any chemical reaction between or among them by virtue of the fact that they are separated from each other by being in separate pills, capsules or gel caps; (b) ease of production of a means to deliver multiple medications simultaneously, by virtue of each pill, capsule or gel cap being capable of being produced with different medications at remote distant locations, before the final assemblage; (c) flexibility, since the content or concentration can be changed for one substance without influencing the chemical properties of the other; (d) increased patient compliance and assurance that the patient is actually taking several medical substances since they come as "one dose"; (e) increased patient compliance because the patient will be more willing to take one pill compared to several; (f) reducing the risk of medication confusion both for the patient and/or the staff at for example nursing homes, hospitals, since there will be fewer pills to kept track of; and (g) a precise "medical" communication, because it shows clearly which products are combined (not mixed), and thus opening the area of "synergy" medicine.

It is contemplated that the inventive concepts herein described may be variously otherwise embodied and it is intended that the appended claims be construed to include alternative embodiments of the invention except only insofar as limited by prior art.

Furthermore, by standardizing the diameter and the shape of the different medication products as described herein, it becomes possible to thereby obtain an optimal physical configuration that favors the swallowing reflex of a live body.

In addition, by standardizing the diameter and the shapes of the different Pills, it becomes possible to customize the medication product delivery device to the individual patient. The dosages can also be individualized by connecting or affixing to each other multiple Pills of the same medication in order to obtain, for example, a double dose.

Also by standardizing the diameter and the shape of the various Pills, the invention allows for putting multiple medications into a multiple medication assemblage, which is perceived by the patient as being "one" Pill, rather than the otherwise need for the patient to be required to use several Pills to achieve medication compliance.

Another advantage of the invention is that by standardizing the diameter and the shape of the various Pills, it becomes possible to build standardized automated feeding machines for an assembly line. The medical prescription coming from a physician can then be translated into the invented customized delivery system, adjusted to the patient's weight, sex, and age, simply by using multiple inner container feeders, each holding different medications. Thus making a means for creating a new international industry consisting of combined assembly line/fulfillment centers/pharmacies that can communicate directly with the physicians or prescription centers all over the world, to produce these individualized multi medication devices based upon a single digital classification system merely referring to for example color, ingredient and does or a reference number.

The invention claimed is:

1. A device for the simultaneous delivery of multiple medication products to a live body, with such device comprising:
    a first medication delivery means, wherein the said first medication delivery means is a pill; and
    a second medication delivery means, wherein the said second medication delivery means is a capsule;
    wherein the said first medication delivery means is connected or affixed by connection means to the said second medication delivery means in a chain, train or string fashion; wherein the connection means is a glue.

2. A device for the simultaneous delivery of multiple medication products to a live body, with such device comprising:
    a first medication delivery means, wherein the said first medication delivery means is a pill; and
    a second medication delivery means, wherein the said second medication delivery means is a capsule;
    wherein the said first medication delivery means is removably connected or affixed by connection means to the said second medication delivery means in a chain, train or string fashion; wherein the connection means is a glue.

* * * * *